(12) United States Patent
Powell et al.

(10) Patent No.: US 12,213,648 B2
(45) Date of Patent: Feb. 4, 2025

(54) MEDICAL DEVICES AND RELATED METHODS

(71) Applicant: Boston Scientific Scimed, Inc., Maple Grove, MN (US)

(72) Inventors: Sean Powell, Holden, MA (US); Bryan Dillon, Jefferson, MA (US); Jan Weber, Maastricht (NL); Martyn Folan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 184 days.

(21) Appl. No.: 17/663,933

(22) Filed: May 18, 2022

(65) Prior Publication Data

US 2022/0369901 A1 Nov. 24, 2022

Related U.S. Application Data

(60) Provisional application No. 63/190,267, filed on May 19, 2021.

(51) Int. Cl.
*A61B 1/005* (2006.01)
(52) U.S. Cl.
CPC .......... *A61B 1/0052* (2013.01); *A61B 1/0057* (2013.01)
(58) Field of Classification Search
CPC . A61B 1/0052; A61B 1/0057; A61B 1/00042; A61B 1/00066; A61B 1/0008; A61B 1/00098; A61B 1/00101; A61B 1/00; A61B 1/005; A61B 1/0051; A61B 1/008; A61B 1/0055

(Continued)

(56) References Cited

U.S. PATENT DOCUMENTS

| 4,865,109 A | 9/1989 | Sherman |
| 5,507,374 A | 4/1996 | Rude |

(Continued)

FOREIGN PATENT DOCUMENTS

| CN | 112438686 | | 3/2021 | |
| CN | 112438686 A | * | 3/2021 | ......... A61B 1/00066 |
| JP | H06217928 | | 8/1994 | |

OTHER PUBLICATIONS

M-Series Standard Clutch Manual Roller Shades, Patrician, Web, https://patricianwindowcoverings.com/m-series-standard-clutch-manual-roller-shades (4 pages).

(Continued)

*Primary Examiner* — Ryan N Henderson
*Assistant Examiner* — Pamela F Wu
(74) *Attorney, Agent, or Firm* — Bookoff McAndrews, PLLC

(57) ABSTRACT

A medical device includes a handle including an axle, a device shaft extending from the handle to a distal end, and a control device. The control device is coupled to the handle, and the control device includes a knob. The knob is rotatable relative to the handle. The control device also includes a control shaft extending from the knob, at least one spring clutch including two legs, and a spool. The spool is rotatable relative to the axle. The control device also includes one or more wires coupled to the spool. Rotation of the knob is configured to rotate the control shaft, causing the at least one spring clutch to loosen, the spool to rotate, and the one or more wires to move.

20 Claims, 6 Drawing Sheets

(58) Field of Classification Search
USPC .................................................. 600/146, 149
See application file for complete search history.

(56) References Cited

U.S. PATENT DOCUMENTS

| | | | |
|---|---|---|---|
| 9,101,269 B2 | 8/2015 | Selkee | |
| 2017/0114575 A1* | 4/2017 | Cumbo | ................... E05B 77/54 |
| 2019/0353210 A1* | 11/2019 | Custer | ................... F16D 13/757 |
| 2021/0212556 A1 | 7/2021 | Nguyen et al. | |
| 2022/0095893 A1* | 3/2022 | Weldon | .............. A61B 1/00078 |

OTHER PUBLICATIONS

International Search Report and Written Opinion issued in International Application No. PCT/US2022/072396, issued Sep. 8, 2022 (27 pages).

* cited by examiner

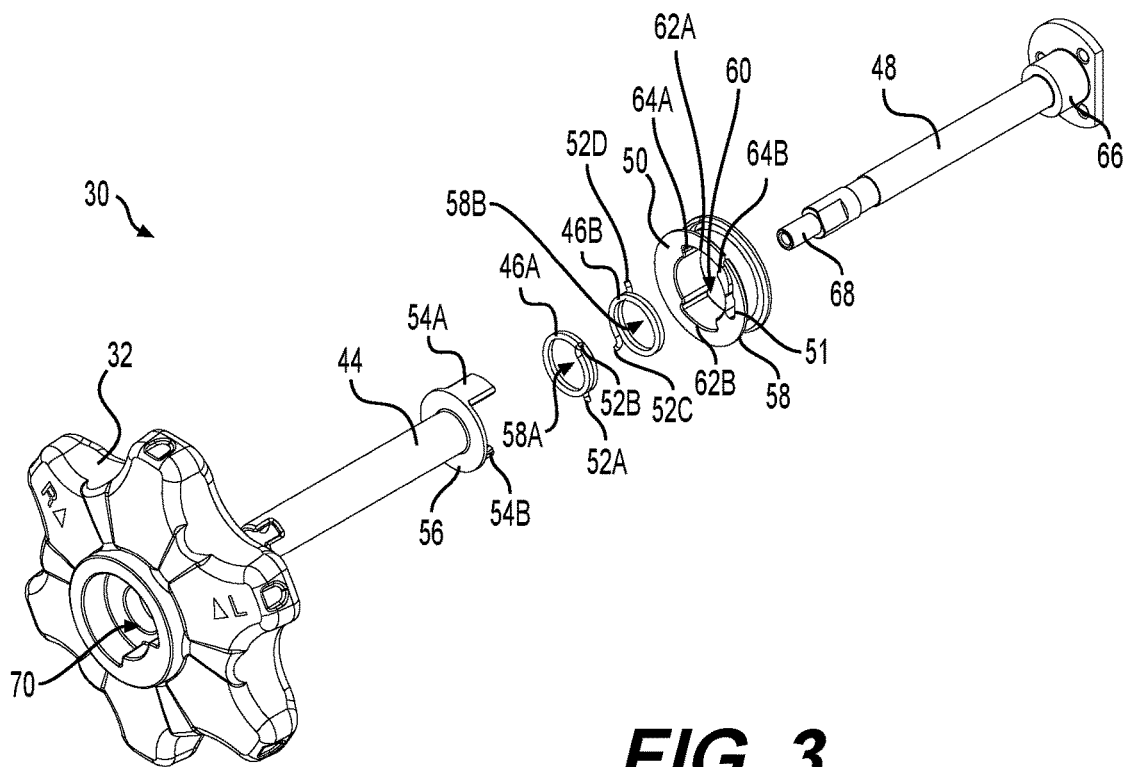
FIG. 3
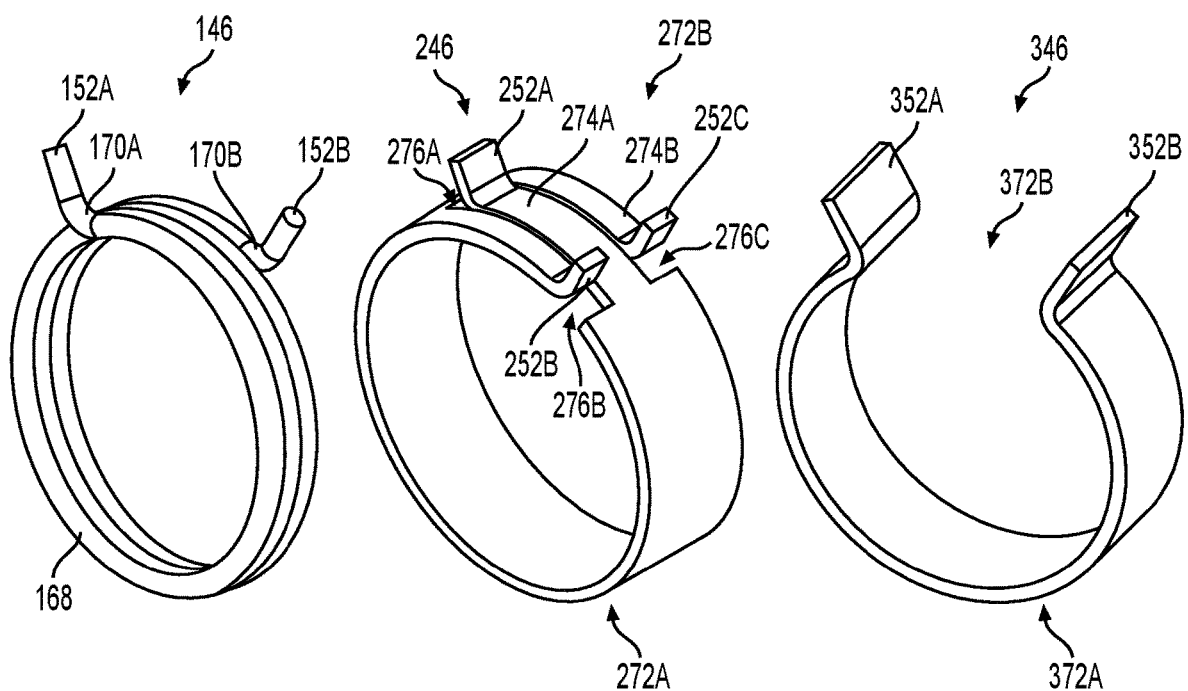
FIG. 4A  FIG. 4B  FIG. 4C

MEDICAL DEVICES AND RELATED METHODS

CROSS-REFERENCE TO RELATED APPLICATIONS

This patent application claims the benefit under 35 U.S.C. § 119 to U.S. Provisional Patent Application No. 63/190,267, filed on May 19, 2021, the entirety of which is incorporated herein by reference.

TECHNICAL FIELD

Various aspects of this disclosure generally relate to medical devices and methods for accessing, viewing, manipulating, or otherwise treating tissue or other material within a body. In particular, aspects of the disclosure relate to medical devices and methods for controlling the locking and unlocking of deflection or other movement of a portion of a delivery shaft of the medical device.

BACKGROUND

In certain medical procedures, physicians, technicians, or other users need to control a duodenoscope (or other scope or medical device) and other medical accessory devices. Depending on a patient's position relative to that of the user's position, the user controlling the device may need to contort and/or twist the user's wrists and/or body so that the medical device is adjusted and positioned to face an intended target site. As a result, users may be at an increased risk to suffer ergonomic injuries to their hands, wrists, and back. Furthermore, a distal end of the medical device may be deflectable in one or more directions. The deflection may be locked, for example, via a proximal locking element, but smaller or more controlled movements may require the locking element to be disengaged and then re-engaged. Alternatively, the user may attempt to deflect or otherwise maneuver the medical device with the locking element engaged. These movements may further increase the user's risks to suffer ergonomic injuries. These concerns may increase the duration, costs, and risks of the medical procedure. The devices and methods of this disclosure may rectify some of the deficiencies described above or address other aspects of the art.

SUMMARY

Examples of this disclosure relate to, among other things, devices and methods for controlling the locking and unlocking of deflection or other movement of a portion of a shaft. Each of the examples disclosed herein may include one or more of the features described in connection with any of the other disclosed examples.

In one example, a medical device may include a handle including an axle, a device shaft extending from the handle to a distal end, and a control device. The control device may be coupled to the handle, and the control device may include a knob. The knob may be rotatable relative to the handle. The control device also may include a control shaft extending from the knob, at least one spring clutch including two legs, and a spool. The spool may be rotatable relative to the axle. The control device also may include one or more wires coupled to the spool. Rotation of the knob may be configured to rotate the control shaft, causing the at least one spring clutch to loosen, the spool to rotate, and the one or more wires to move.

The medical device may include one or more of the following features. The shaft may include a radial extension, and the shaft may include first and second projections extending from the radial extension. The spool may define first and second gaps, and the first and second projections may be configured to be positioned within the first and second gaps. The at least one spring clutch may include first and second spring clutches, and the first and second spring clutches each may include first and second legs. Rotation of the knob in a first direction may cause the first projection to contact a first leg of the first spring clutch to loosen the first spring clutch, and rotation of the knob in the first direction may cause the second projection to contact a first leg of the second spring clutch to loosen the second spring clutch. Further rotation of the knob in the first direction may cause (1) the first leg of the first spring clutch to contact a first stop surface of the spool adjacent the first gap, (2) the first leg of the second spring clutch to contact a second stop surface of the spool adjacent the second gap, and (3) the spool to rotate in the first direction. Rotation of the knob in a second direction may cause the first projection to contact a second leg of the second spring clutch to loosen the second spring clutch, and rotation of the knob in the second direction may cause the second projection to contact a second leg of the first spring clutch to loosen the first spring clutch. Further rotation of the knob in the second direction may cause (1) the second leg of the second spring clutch to contact a third stop surface of the spool adjacent the second gap, (2) the second leg of the first spring clutch to contact a fourth stop surface of the spool adjacent the second gap, and (3) the spool to rotate in the second direction.

The at least one spring clutch may include at least one spring formed of a coil with two radially outward extending legs. The at least one spring clutch may include at least one spring with a ring-like shape that includes a partially cylindrical portion and an interaction portion. The interaction portion may include a first end and a second end. The first end may include a first radially outward extending leg, and the second end may include two radially outward extending legs. The spring clutch may include at least one spring with a partial ring-like shape that includes a partially cylindrical portion and an open portion. The partially cylindrical portion may include two radially outward extending legs on opposing sides of the open portion. The spring clutch may include at least one spring formed of a coil with two radially inward extending legs.

The control device may be a first control device. The medical device may further include a second control device that is coaxial with the first control device. The second control device may include a second knob, and the second knob may be rotatable relative to the handle. The second control device may also include a second control shaft extending from the second knob, at least one second spring clutch including two legs, and a second spool. The second spool may be rotatable relative to the axle. The second control device may further include one or more second wires coupled to the second spool. Rotation of the second knob may be configured to rotate the second control shaft, causing the at least one second spring clutch to loosen, the second spool to rotate, and the one or more second wires to move. A portion of the control shaft of the first control device may be nested within the second control shaft of the second control device. The medical device may further include a hollow axle separating a portion of the control shaft from the second control shaft. The hollow axle may be coupled to the handle, and the hollow axle may include a radial extension that separates the spool of the first control device from the second spool of the second control device. The distal end of the delivery shaft may be deflectable via the control device. The handle may include at least one port configured to receive a medical device. The port may be connected to a lumen that extends through the handle and the delivery shaft. The control device may be configured to control an elevator positioned adjacent to the lumen at the distal end of the delivery shaft. The control device may be positioned on a proximal portion of the handle, and the medical device may not include a brake external to a body of the handle to lock the position of the knob.

In another aspect, a medical device may include a handle, including an axle. The medical device may also include a device shaft extending from the handle to a distal end, and a control device. The control device may be coupled to the handle and may include a first knob. The first knob may be rotatable relative to the handle. The control device may also include a first control shaft extending from the first knob, at least one first spring clutch including two legs, a first spool that may be rotatable relative to the axle, and one or more first wires coupled to the first spool. The control device may also include a second knob. The second knob may be rotatable relative to the handle. The control device may include a second control shaft extending from the second knob, at least one second spring clutch including two legs, a second spool that may be rotatable relative to the axle, and one or more second wires coupled to the second spool. Rotation of the first knob may be configured to rotate the first control shaft, causing the at least one first spring clutch to loosen, the first spool to rotate, the one or more first wires to move, and the distal end of the delivery shaft to deflect in a first plane. Rotation of the second knob may be configured to rotate the second control shaft, causing the at least one second spring clutch to loosen, the second spool to rotate, the one or more second wires to move, and the distal end of the delivery shaft to deflect in a second plane different from the first plane.

The medical device may include one or more of the following features. The first shaft may include at least one first projection, and the second shaft may include at least one second projection. The first spool may define at least one first gap, and the second spool may define at least one second gap. The at least one first projection may be positioned within the at least one first gap, and the at least one second projection may be positioned within the at least one second gap. The legs of the at least one first spring clutch may be positioned between the at least one first projection and edges of the at least one first gap. The legs of the at least one second spring clutch may be positioned between the at least one second projection and edges of the at least one second gap. The first plane and the second plane may be perpendicular.

In yet another aspect, a medical device handle may include an axle and a control device. The axle may be fixed to the handle. The control device may include a first knob that may be rotatable relative to the handle, a first control shaft extending from the first knob, at least one first spring clutch including two legs, a first spool that may be rotatable relative to the axle, and one or more first wires coupled to the first spool. The control device may also include a second knob that may be rotatable relative to the handle, a second control shaft extending from the second knob, at least one second spring clutch including two legs, a second spool that may be rotatable relative to the axle, and one or more second wires coupled to the second spool. Rotation of the first knob may be configured to rotate the first control shaft, causing the at least one first spring clutch to loosen, the first spool to rotate, and the one or more first wires to move. Rotation of the second knob may be configured to rotate the second control shaft, causing the at least one second spring clutch to loosen, the second spool to rotate, and the one or more second wires to move.

The medical device handle may include one or more of the following features. A portion of the first control shaft may be nested within the second control shaft. The medical device handle may further include a hollow axle separating a portion of the first control shaft from the second control shaft. The hollow axle may be coupled to the handle and may include a radial extension that separates the first spool from the second spool.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 3 illustrates an exploded view of the control device, according to aspects of this disclosure.

FIGS. 4A-4D illustrate different exemplary spring clutches that may be incorporated in the control device of FIGS. 1A-1C, 2A-2C, and 3, according to aspects of the disclosure.

DETAILED DESCRIPTION

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Examples of this disclosure include devices and methods for facilitating and/or improving the efficacy, efficiency, and/or safety of a medical procedure. Embodiments of the disclosure may relate to devices and methods for performing various medical procedures and/or treating portions of the large intestine (colon), small intestine, cecum, esophagus, stomach, any other portion of the gastrointestinal tract, kidney or other portion of the urinary tract, heart, lungs, and/or any other suitable patient anatomy. Various embodiments described herein include single-use or disposable medical devices. Some aspects of the disclosure may be used in performing an endoscopic, arthroscopic, bronchoscopic, ureteroscopic, colonoscopic, or other type of procedure. For example, the disclosed aspects may be used with duodenoscopes, bronchoscopes, ureteroscopes, colonoscopes, catheters, diagnostic or therapeutic tools or devices, or other types of medical devices. One or more of the elements discussed herein could be metallic, plastic, or include a shape memory metal (such as nitinol), a shape memory polymer, a polymer, or any combination of biocompatible materials.

Reference will now be made in detail to examples of the disclosure described above and illustrated in the accompanying drawings. Wherever possible, the same reference numbers will be used throughout the drawings to refer to the same or like parts. It is noted that one or more aspects of the medical devices discussed herein may be combined and/or used with one or more aspects of other medical devices discussed herein.

Figure 1A:
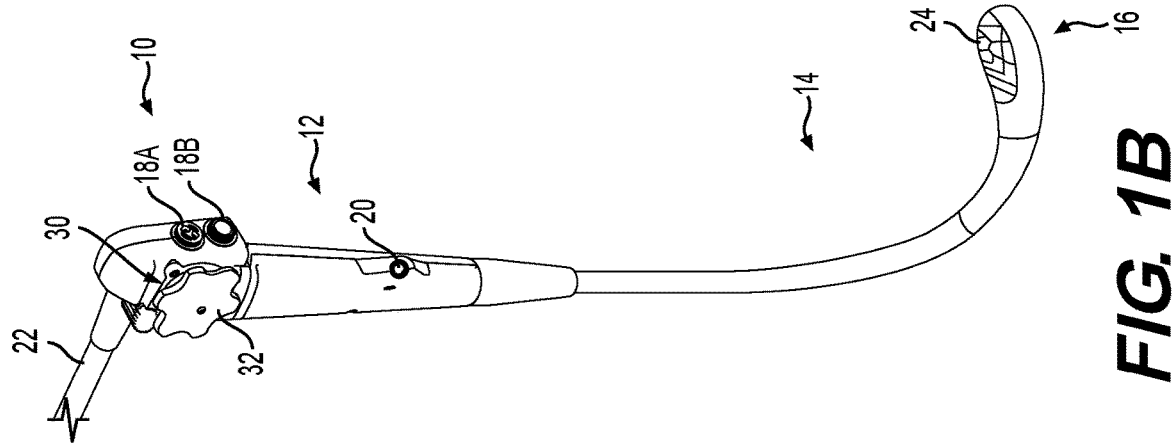
FIGS. 1A-1C illustrate different views of an exemplary medical device, according to aspects of this disclosure.
Figure 1B:
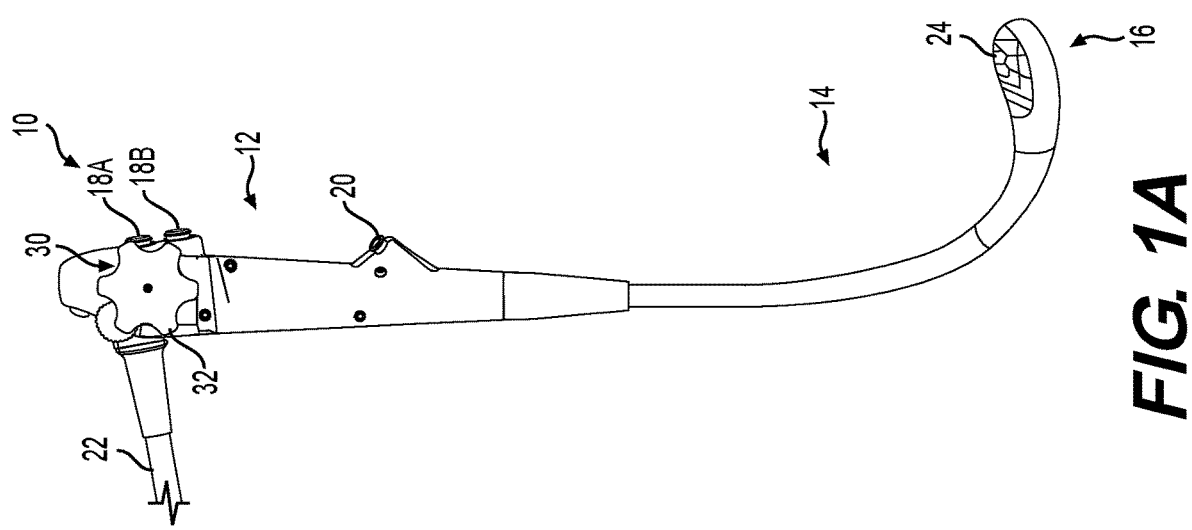
Figure 1C:
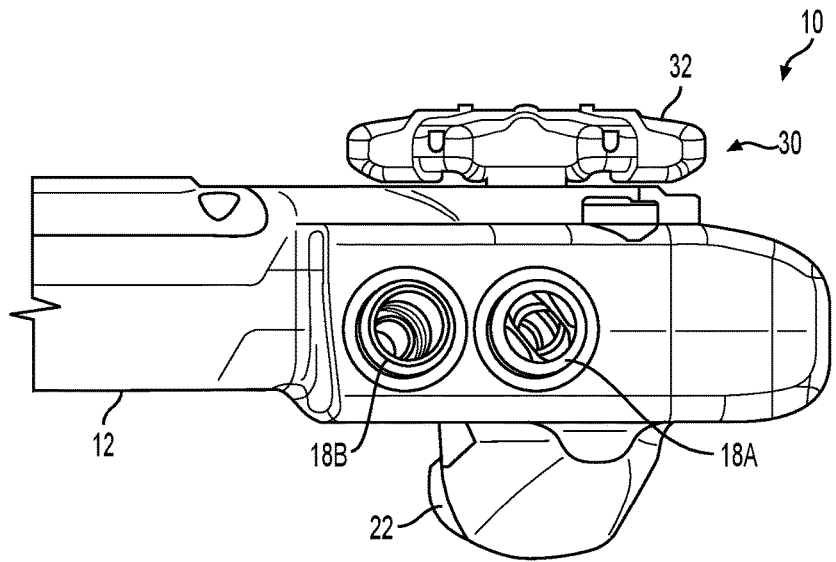

FIGS. 1A-1C illustrate different views of an exemplary medical device 10. FIG. 1A is a front view of medical device 10, and FIG. 1B is a perspective view of medical device 10. FIG. 1C is a side view of a proximal portion of medical device 10. Medical device 10 includes a handle 12, including a handle body, and a device shaft or a delivery shaft 14 extending from handle 12 to a distal end 16. Medical device 10 may be a duodenoscope, an endoscope, a colonoscope, an ureteroscope, a bronchoscope, etc., or any other like medical device having a handle and a shaft. Additionally, medical device 10 includes a control device 30. Control device 30 is movable (e.g., rotatable) relative to handle 12, and may control the movement of a portion (e.g., distal end 16) of delivery shaft 14.

Handle 12 may include one or more apertures 18A and 18B, for example, on a proximal portion of handle 12. One or more of apertures 18A and 18B may be couplable to or receive one or more valves, for example, to control the delivery of air or water, or the application of suction through handle 12 and delivery shaft 14.

Additionally, handle 12 may have one or more lumens (not shown) that communicate with one or more lumens of delivery shaft 14, for example, extending to distal end 16. In this aspect, handle 12 may include at least one port 20, for example, in an intermediate portion (e.g., between proximal and distal portions) of handle 12. Port 20 may open into the one or more working channels or lumens in handle 12. Port 20 may receive one or more tools or end effectors, and the one or more tools or end effectors may be delivered through handle 12 and delivery shaft 14, for example, out of distal end 16. In this aspect, port 20 may be sized and/or shaped to receive one or more medical devices (e.g., a forceps, a grasper, scissors, a clip, a stapler, a needle, a knife, an electrode, a cautery loop, etc.), and deliver the one or more medical devices to an area proximate to distal end 16 of delivery shaft 14. Additionally, port 20 may be configured to help form a seal around a proximal portion of the medical device, for example, by including a valve, a threading to screw on a cap, etc.

Handle 12 may be coupled to a conduit 22. Conduit 22 may connect handle 12 to an external power source, processing software, one or more displays, one or more memory or storage devices, etc. In this aspect, medical device 10 may include one or more illumination devices and/or cameras at distal end 16, which may be powered and/or connected to processing software, one or more displays, a memory, etc. via one or more communication wires (not shown) within medical device 10 and via conduit 22. Additionally, conduit 22 may connect handle 12 to one or more fluid sources, for example, an air source, a water source, etc. Conduit 22 may also connect handle 12 to a suction source. In these aspects, one or more valves coupled to or received within apertures 18A and 18B may control the delivery of air or water and/or the application of suction through medical device 10 to the area proximate to distal end 16 of delivery shaft 14.

Control device 30 is coupled to handle 12, for example, at a proximal portion of handle 12. As mentioned, control device 30 is movable (e.g., rotatable) relative to handle 12, and may control the movement (e.g., deflection) of distal end 16 of delivery shaft 14. Alternatively, control device 30 may actuate or move an elevator in delivery shaft 14, or otherwise actuate a cable driven function of medical device 10.

Control device 30 may include a dial, wheel, lever, knob 32, or other rotating control element, which may be rotatable to deflect distal end 16 of delivery shaft 14 in a first direction or in a second direction. As shown in FIG. 1C, knob 32 may extend away from handle 12 (e.g., vertically in a side view of handle 12). Moreover, as discussed in detail below, control device 30 may include one or more clutch devices, for example, to help lock and/or unlock the position of knob 32 and thus lock and/or unlock the position of distal end 16 of delivery shaft 14, or other aspect of delivery shaft 14.

Furthermore, distal end 16 of delivery shaft 14 may include at least one distal opening 24, for example, through which a medical device may be extended, fluid may be delivered, suction may be applied, or medical device 10 may otherwise treat the treatment site. Although not shown, distal end 16 may also include one or more apparatuses for lighting (e.g. LED) and imaging (e.g. a camera), an elevator to direct an instrument or medical device exiting distal opening 24, and/or openings for irrigation and/or suction. Moreover, medical device 10 may include one or more additional components (e.g., a processor, a memory, etc.) for controlling the various functions at distal end 16 and/or other portions of medical device 10.

Figure 2A:
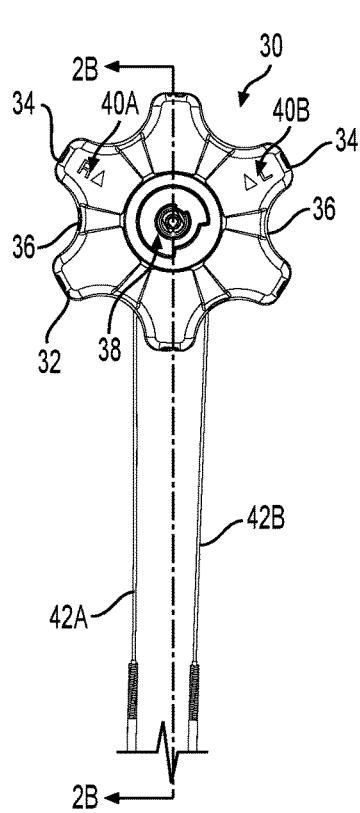
FIGS. 2A-2C illustrate different views of a control device of the medical device of FIGS. 1A-1C, according to aspects of this disclosure.
Figure 2B:
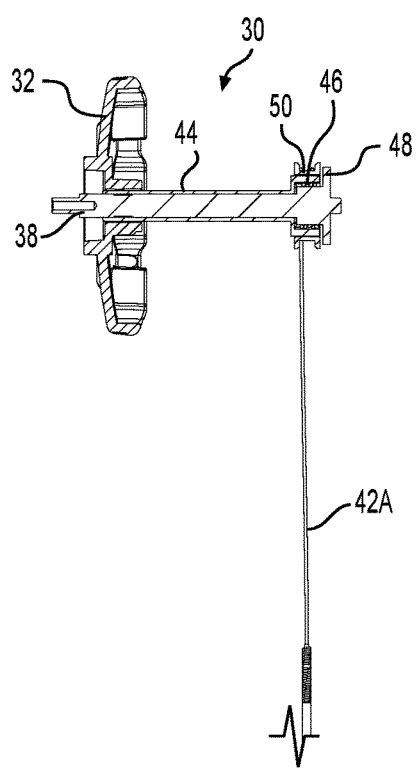
Figure 2C:
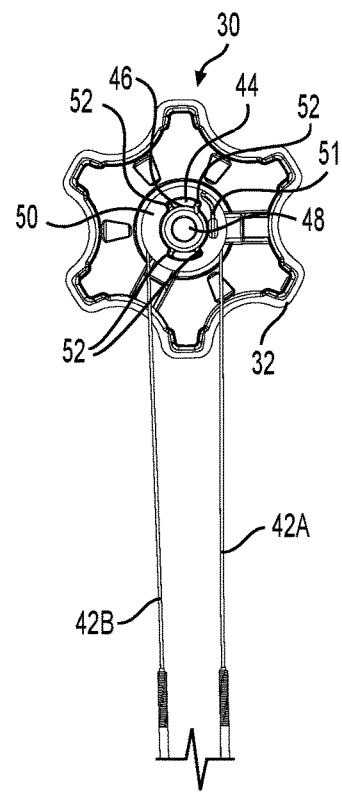

FIGS. 2A-2C illustrate various views of control device 30. FIG. 2A is a front view of control device 30. FIG. 2B is a cross-sectional view of control device 30, for example, along cross-section 2B-2B in FIG. 2A. FIG. 2C is a rear view of control device 30, for example, from a position internal to handle 12 (not shown) when control device 30 is coupled to handle 12. As mentioned, control device 30 includes knob 32. Knob 32 may include one or more protrusions 34 and depressions 36, for example, extending radially away from and radially toward a rotational center 38 of knob 32, respectively. Protrusions 34 and depressions 36 may help a user grip and/or rotate knob 32. Additionally, knob 32 may include one or more indications, for example, a right deflection indication 40A and a left deflection indication 40B. In this aspect, rotation of knob 32 in the direction of right deflection indication 40A (e.g., clockwise) may deflect distal end 16 of delivery shaft 14 to the right, and rotation of knob 32 in the direction of left deflection indication 40B (e.g., counter-clockwise) may deflect distal end 16 of delivery shaft 14 to the left. Alternatively, in other embodiment, rotation of knob 32 in one direction may raise an elevator, and rotation of knob 32 in another direction may lower the elevator.

As shown in FIGS. 2A-2C, control device 30 includes one or more steering or control elements (e.g., linkages, chains, belts, wires, etc.), for example, a first control wire 42A and a second control wire 42B. In at least one aspect, first and second control wires 42A and 42B may extend from knob 32, through handle 12 and delivery shaft 14, to a distal portion (e.g., distal end 16) of delivery shaft 14. In another aspect, first and second control wires 42A and 42B may extend through handle 12 and be coupled to one or more deflection wires or other control elements in delivery shaft 14. In any of these aspects, rotation of knob 32 controls the movement of control wires 42A and 42B, and thus rotation of knob 32 may control the deflection of distal end 16 of delivery shaft 14, the actuation of an elevator, or otherwise actuate a cable driven function of medical device 10.

As shown in FIG. 2B, control device 30 includes a control shaft 44. Shaft 44 may be integrally formed with or otherwise fixedly coupled to knob 32. Shaft 44 may extend internal to a proximal portion of handle 12. Proximal portions of first control wire 42A and second control wire 42B may be indirectly coupled to shaft 44, for example, tightly wrapped around and secured to an element that can be rotatably coupled to shaft 44 (e.g., a spool 50, FIGS. 2B, 2C, and 3). For example, as shown in FIGS. 2C and 3, spool 50 may include a coupling portion 51 (e.g., a slot, gap, opening, etc. to receive a proximal portion of one or more of first control wire 42A and second control wire 42B to secure the control wire(s) to spool 50. It is noted that wire 42B is not shown in FIG. 2B, as wire 42B is outside of the cross-section 2B-2B (FIG. 1). Nevertheless, both control wires 42A and 42B may be coupled to spool 50 such that rotation of spool 50 may control the movement of both control wires 42A and 42B. In this aspect, rotating knob 32 rotates shaft 44, which rotates spool 50, which, in turn, may pull one of first and second control wires 42A and 42B proximally to deflect a distal portion of delivery shaft 14 in a direction. Alternatively, rotating knob 32 may rotate shaft 44, which, in turn through spool 50, may pull one of first and second control wires 42A and 42B proximally to actuate or move an elevator in delivery shaft 14, or otherwise actuate a cable driven function of medical device 10. Furthermore, although not shown, control device 30 may include one or more gears, sprockets, pulleys, cranks, etc. Control device 30 may also include one or more racks, chains, belts, linkages, etc.

Moreover, as shown in FIGS. 2B and 2C, control device 30 includes at least one biasing device, for example, at least one spring clutch 46. Spring clutch 46 may be at least partially circular, and surrounds a rod or axle 48. Axle 48 may be fixed relative to handle 12. Additionally, as shown in FIG. 2C, spring clutch 46 may be positioned around axle 48, for example, between axle 48 and spool 50. When no forces are acting on control device 30, spring clutch 46 is tightly positioned or pressed around axle 48, and helps to secure spool 50, and thus first and second control wires 42A and 42B, relative to axle 48, and thus relative to handle 12 and delivery shaft 14. In one or more aspects, spring clutch 46 may help to lock, retain, or otherwise constrain the movement of axle 48, and thus first and second control wires 42A and 42B, for example, via a frictional connection between spring clutch 46 and axle 48.

Spring clutch 46 may include one or more legs 52. Rotating knob 32 and shaft 44 may interact with one or more of legs 52 of spring clutch 46. For example, rotating knob 32 and shaft 44 may cause a portion of shaft 44 to contact one or more of legs 52, pushing one or more of legs 52 in a direction to unwrap, expand, or loosen spring clutch 46. Loosening spring clutch 46 may reduce a frictional connection between spool 50 and axle 48. Furthermore, rotating knob 32 and shaft 44 may also cause a portion of shaft 44, or a portion of the one or more legs 52, to contact a portion of spool 50, which may cause spool 50 to rotate. Rotating spool 50 may then proximally retract one or more of control wires 42A and 42B to control a portion of delivery shaft 14, for example, to deflect distal end 16.

As will be explained in detail below, when forces are no longer acting on knob 32, spring clutch 46 contracts, and helps to secure spool 50 relative to shaft 48. Because spring clutch 46 is in the loosened position when spool 50 is rotated, spring clutch 46 does not provide a spring back force to urge spool 50 back toward the original position before the rotation. Accordingly, spring clutch 46 helps to lock spool 50 in the rotated position. In this aspect, spring clutch 46 helps to secure spool 50, and thus first and second control wires 42A and 42B, in the position selected by the user acting on knob 32. For example, securing spool 50 in a selected position may help to secure distal end 16 in a deflected or articulated position. In this aspect, securing spool 50 in the selected position may help to lock or otherwise hold distal end 16 in a selected configuration (e.g., a manipulated position), for example, relative to other portions of delivery shaft 14 and/or relative to the treatment site. As will be discussed below, if first or second control wires 42A or 42B are pulled distally (e.g., by inherent forces from a portion of delivery shaft 14 bending or being deflected, by a portion of delivery shaft 14 contacting tissue or other material, etc.), first or second control wires 42A or 42B may thus impart force(s) to spool 50. The force(s) may cause spool 50 to interact with one or more of legs 52 of spring clutch 46 and may cause spring clutch 46 to tighten, and thus help to more securely secure spool 50 to axle 48, preventing relative rotation.

FIG. 3 is an exploded view of control device 30, including knob 32, shaft 44, at least one spring clutch (i.e., two spring clutches 46A and 46B), axle 48, and spool 50. Although not shown, control wires 42A and 42B may be coupled to spool 50. In this aspect, rotating knob 32 and shaft 44 may rotate spool 50, which may control the movement of control wires 42A and 42B (FIGS. 2A-2C) to deflect or otherwise control a distal portion of the delivery shaft (not shown).

As shown, a portion of shaft 44 internal to handle 12 includes at least one projection. As shown in FIG. 3, shaft 44 may include two projections 54A and 54B, for example, with each projection 54A, 54B on opposing sides of shaft 44, for example, on opposing sides relative to a longitudinal axis of shaft 44. Shaft 44 may also include a radial extension 56, for example, that extends radially outward from a longitudinal portion of shaft 44 (e.g., at an end of shaft 44 opposite to knob 32). In this aspect, projections 54A, 54B may extend longitudinally from radial extension 56. Additionally, spring clutches 46A and 46B are each formed by wire coils with openings 58A and 58B, and each includes two legs 52A and 52B, and 52C and 52D, for example, projecting radially away from the at least partially cylindrical spring clutches 46A and 46B, respectively. In this aspect, spring clutch 46A includes two legs 52A and 52B, and spring clutch 46B includes two legs 52C and 52D.

Spool 50 may include a generally cylindrical outer portion 58. Moreover, spool 50 may include a generally cylindrical inner opening 60, for example, to receive axle 48, and inner opening 60 may include two widened portions or gaps 62A and 62B. For example, gap 62A may include a first stop surface 64A and a second stop surface 64B on opposing ends of gap 62A. In this aspect, and as discussed below, when knob 32 and shaft 44 are rotated, projections 54A, 54B may interact with legs 52A-52D and gaps 62A, 62B. Moreover, although not shown, control device 30 may include additional spring clutches, for example, in order to modify the frictional forces generated between the one or more spools 50 and axle 48. Additionally, control device 30 may include additional projections from shaft 44, gaps in spool 50, etc. in order to accommodate and actuate the legs of the additional spring clutches.

Referring to FIGS. 2B, 2C, and 3, when control device 30 is assembled, axle 48 is fixedly coupled to a portion of handle 12. Spring clutches 46A and 46B and spool 50 may be positioned around a portion of axle 48. For example, axle 48 may include a widened portion 66. Openings 58A and 58B of spring clutches 46A and 46B may be positioned over widened portion 66, for example, laterally spaced along widened portion 66. When spring clutches 46A and 46B are positioned over widened portion 66, spring clutches 46A and 46B may be tightly positioned around widened portion 66. For example, spring clutches 46A and 46B may be loosened (e.g., but pinching or otherwise bringing one or more of legs 52A-52D of each spring clutch 46A and 46B toward each other) in order to be positioned around widened portion 66. Spool 50 may be positioned over spring clutches 46A and 46B, and also around widened portion 66 of axle 48.

Then, shaft 44 may be positioned over axle 48. For example, as shown in FIG. 2B, shaft 44 includes an inner lumen, which receives axle 48. Axle 48 may include a coupling portion 68, and knob 32 may include an opening 70, for example connected to the lumen in shaft 44. In this aspect, a coupling element (e.g., a screw, a bolt, etc.) may be used to couple axle 48 to knob 32, yet allow relative rotation between them.

When shaft 44 is positioned over axle 48, radial extension 56 may abut or be adjacent to widened portion 66 of axle 48. Furthermore, projections 54A and 54B may be positioned between pairs of legs 52A-52D of spring clutches 46A and 46B and within gaps 62A and 62B. For example, projection 54A may be positioned between leg 52B of spring clutch 46A and leg 52D of spring clutch 46B, and also within gap 62A. Additionally, projection 54B may be positioned between leg 54A of spring clutch 46A and leg 52C of spring clutch 46B, and also within gap 62B.

When control device 30 is assembled, rotating knob 32, and thus shaft 44, in a first direction, for example, clockwise, may cause projection 54A to contact leg 52B of spring clutch 46A and push leg 52B clockwise. This contact may also rotate the entirety of spring clutch 46A, for example, bringing leg 52B of spring clutch 46A into abutting contact with stop surface 64B of gap 62A. Further rotation of knob 32 may cause spring clutch 46A to loosen such that spool 50 is not rotatably fixed relative to axle 48 by spring clutch 46A. Additionally, rotating knob 32 and shaft 44 in the first direction may also cause projection 54B to contact leg 52C of spring clutch 46B and push leg 52C clockwise. This contact may also rotate the entirety of spring clutch 46B, for example, bringing leg 52C of spring clutch 46B into abutting contact with a stop surface of gap 62B. The further rotation of knob 32 may cause spring clutch 46B to loosen such that spool 50 is not rotatably fixed relative to axle 48 by spring clutch 46B.

Conversely, rotating knob 32, and thus shaft 44, in a second direction, for example, counter-clockwise, may cause projection 54A to contact leg 52D of spring clutch 46B and push leg 52D counter-clockwise. This contact may also rotate the entirety of spring clutch 46B, for example, bringing leg 52D of spring clutch 46D into abutting contact with stop surface 64A of gap 62A. Further rotation of knob 32 may cause spring clutch 46B to loosen such that spool 50 is not rotatably fixed relative to axle 48 by spring clutch 46B. Additionally, rotating knob 32 and shaft 44 in the second direction may also cause projection 54B to contact leg 52A of spring clutch 46A and push leg 52A counter-clockwise. This contact may also rotate the entirety of spring clutch 46A, for example, bringing leg 52A of spring clutch 46A into abutting contact with a stop surface of gap 62B. The further rotation of knob 32 may cause spring clutch 46A to loosen such that spool 50 is not rotatably fixed relative to axle 48 by spring clutch 46A.

With both spring clutch 46A and 46B loosened, rotation of knob 32 and shaft 44 may rotate spool 50, and thus control the movement of at least one of first control wire 42A and/or second control wire 42B (FIGS. 2A-2C). Additionally, as mentioned above, external force, for example, forces imparted on spool 50 by the control wires may rotate spool 50 to contact one or more of clutch springs 46A, 46B in such a way to tighten the one or more of clutch springs 46A, 46B. For example, if a force from one of the control wires acts on spool 50 to rotate spool 50 clockwise, then stop surface 64A may contact leg 52D and push leg 52D clockwise, which tightens spring clutch 48B. Similarly, the clockwise force acting on spool 50 may also cause a stop surface of gap 62B to contact leg 52A and push leg 52A clockwise, which tightens spring clutch 48A. As such, control device 30 may also help to retain a portion of delivery shaft 14 in a manipulated position.

Figure 4D:
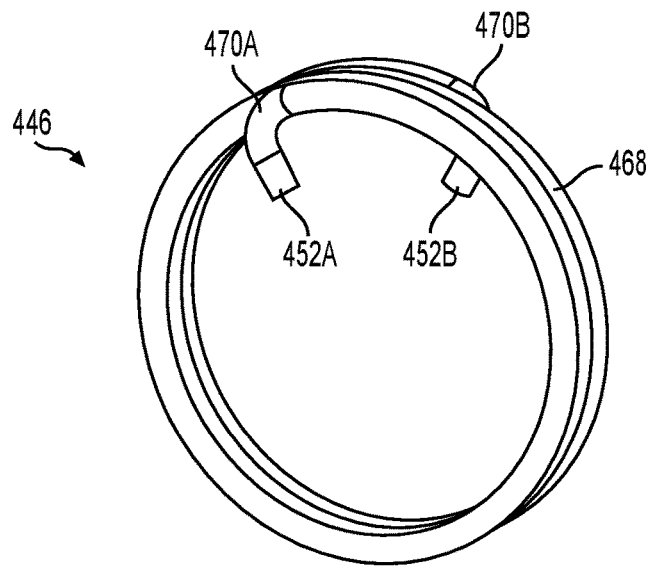

FIGS. 4A-4D illustrate various spring clutches that may be incorporated in control device 30, for example, selectively rotationally coupling and uncoupling spool 50 from axle 48 based on the rotation of knob 32 and shaft 44. As shown in FIG. 4A, a spring clutch 146 includes a coil 168 of wound wire. Additionally, as discussed above, spring clutch 146 includes two legs 152A and 152B that extend radially away from coil 168. Legs 152A and 152B may be connected to coil 168 by bent portions 170A and 170B. As shown, coil 168 may include approximately three loops of wire. However, although not shown, coil 168 may include fewer or more loops of wire, which may affect the amount of force necessary to compress spring clutch 146, and may also affect the holding force applied by spring clutch 146 that retains a spool relative to an axle. As discussed above, a projection from the shaft may interact with legs 152A and 152B to loosen spring clutch 146.

FIG. 4B illustrates another exemplary spring clutch 246. As shown, spring clutch 246 may include a ring-like shape, for example, including an at least partially cylindrical portion 272A and an interaction portion 272B. Interaction portion 272B includes a first end 274A and a second end 274B, which at least partially overlap, for example, along a portion of a circumference of spring clutch 246. First end 274A may include a leg 252A that extends radially outward. Second end 274B may include two legs 252C and 252D, which are spaced apart to form an opening that movably receives first end 274A. As such, first end 274A and second end 274B are movable relative each other. For example, there may be a spacing 276A between leg 252A and one end of cylindrical portion 272A. Additionally, there may be spacings 276B and 276C between legs 252B and 252C and the other end of cylindrical portion 272A. In this aspect, leg 252A may move within spacing 276A. Furthermore, legs 252B and 252C may move within spacings 276B and 276C. As discussed above, a projection from the shaft may interact with one or more of legs 252A, 252B, or 252C to loosen spring clutch 246. Spring clutch 246 may be formed of a sheet metal. Alternatively, spring clutch 246 may be formed of a plastic material, for example, via an injection molding process.

FIG. 4C illustrates yet another exemplary spring clutch 346. As shown, spring clutch 346 may include a partial ring-like shape, for example, including an at least partially cylindrical portion 372A and an open portion 372B. Open portion 372B may extend between a first leg 352A and a second leg 352B. As discussed above, a projection from the shaft may interact with one or more of legs 352A or 352B to loosen spring clutch 346. As with spring clutch 246, spring clutch 346 may be formed of a sheet metal, or, alternatively, spring clutch 346 may be formed of a plastic material, for example, via an injection molding process.

FIG. 4D illustrates a further exemplary spring clutch 446. As shown, spring 446 may also be formed of a coil 468 of wound wire. Spring clutch 446 also includes two legs 452A and 452B that extend radially inward from coil 468. Legs 452A and 452B may be connected to coil 468 by bent portions 470A and 470B. In this aspect, although not shown, spring 446 may be used for a control device that includes an outer cylinder fixed to a housing of the handle (similar to axle 48) and a spool positioned within the opening of the outer cylinder. Rotation of a knob and a shaft may interact with legs 452A and 452B to selectively loosen spring 346 and rotate the internal spool. Furthermore, one or more of spring clutches 46, 46A, 46B, 146, 246, and 346 may be modified to include respective legs extending radially inward.

In these aspects, one or more of spring clutches 46, 46A, 46B, 146, 246, 346, and 446 may be incorporated in control device 30. For example, the desired compression force of the spring, the production costs, and other factors may be considered when selecting the one or spring clutches for control device 30. Additionally, the compression force of control device 30 may be modified by adding or removing one or more spring clutches (or modifying one or more spring clutches, for example, by adding loops of a coil) to the assembly that couples spool 50 to axle 48. Moreover, the compression force of control device 30 may be modified by modifying a diameter of axle 48 that is positioned within the spring clutch(es). The compression force of control device 30 may also be modified by modifying material and/or frictional properties of control device 30. For example, axle 48 may be formed of a Teflon coated shaft. Alternatively or additionally, the spring clutches may be formed of Teflon coated wires or of a plastic that contains Teflon. Furthermore, in one or more aspects, one or more friction reducing agents (e.g., a grease) may be added to one or more surfaces within control device 30.

Additionally, as discussed below, more than two control devices 30 may be used, for example, with nested knobs and hollow tubes or shafts. Furthermore, although two control wires 42A and 42B are shown being coupled to each spool 50, this disclosure is not so limited. For example, one control wire may be coupled to each spool 50, or more than two control wires may be coupled to each spool 50, for example, to provide additional proximal retraction force on one or more portions of delivery shaft 14. Moreover, although two spring clutches 46 are shown coupling each spool 50 to axle 48, this disclosure is not so limited. For example, one spring clutch 46 may be used with each spool 50, or more than two spring clutches 46 may be used with each spool 50, for example, to control the friction force that selectively couples spool 50 to axle 48. The size, materials, stiffness, elasticity, etc. of spring clutches 46, along with the number of spring clutches 46, may be modified as desired to control the frictional coupling between spool 50 and axle 48.

Figure 5A:
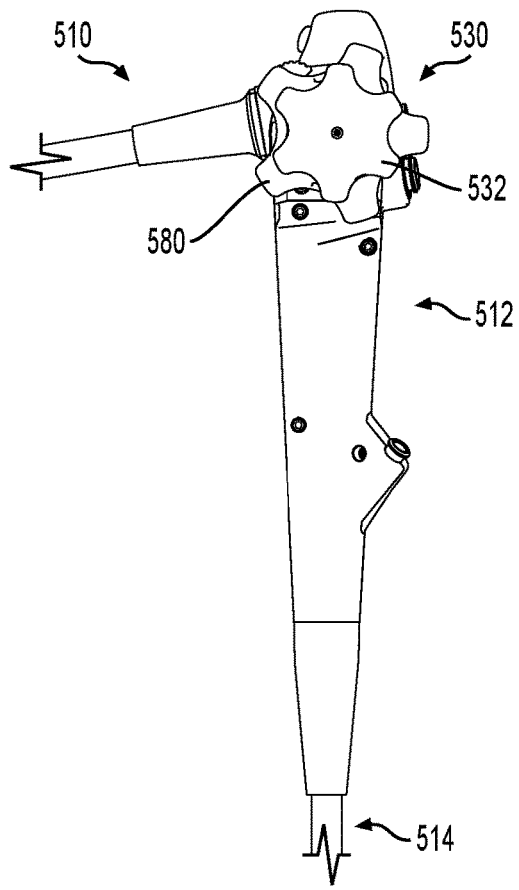
FIGS. 5A-5C illustrate different views of another exemplary medical device, according to aspects of this disclosure.
Figure 5B:
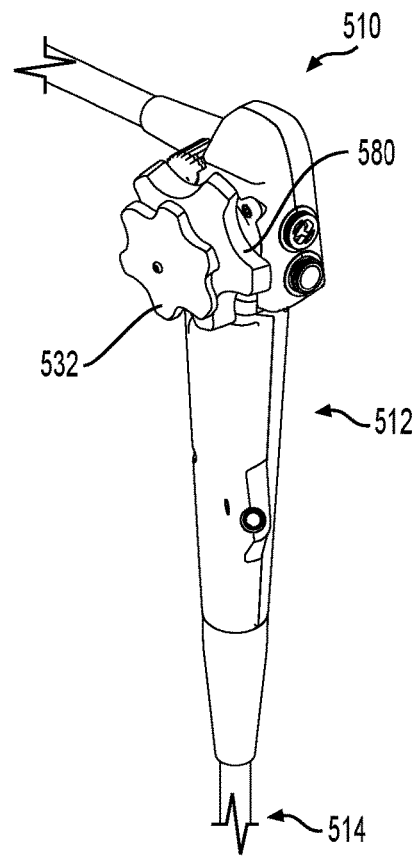
Figure 5C:
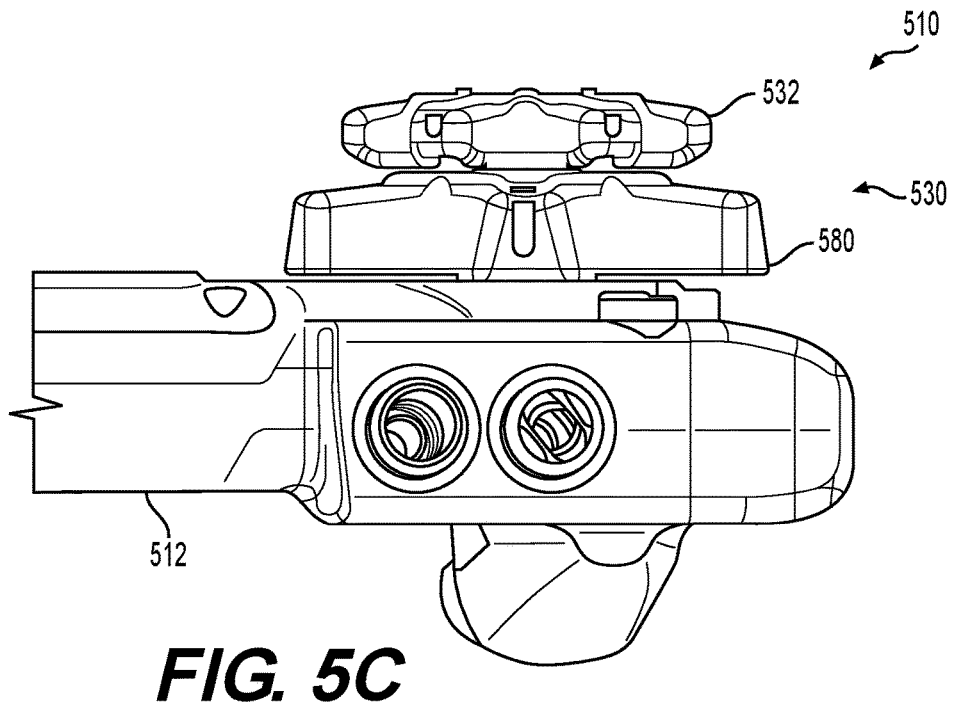

FIGS. 5A-5C illustrate different views of an alternative exemplary medical device 510, according to the disclosure. FIGS. 5A-5C illustrate similar elements to medical device 10 shown by 500 added to the reference numbers. FIG. 5A is a front view of medical device 510, and FIG. 5B is a perspective view of medical device 510. FIG. 5C is a side view of a proximal portion of medical device 510. Medical device 510 includes a handle 512, including a handle body, and a delivery shaft 514 extending from handle 512 to a distal end (not shown). Additionally, medical device 510 includes a control device 530.

Control device 530 includes a first knob 532 and a second knob 580. Second knob 580 may be positioned between first knob 532 and handle 512. In this aspect, first knob 532 may be rotatable relative to handle 512 to actuate or control a distal portion of delivery shaft 514 in a first aspect, and second knob 580 may be rotatable relative to handle 512 to actuate or control a distal portion of delivery shaft 514 in a second aspect. First knob 532, second knob 580, and their respective connections may be substantially coaxial. In one aspect, first knob 532 may control a first elevator within delivery shaft 514, and second knob 580 may control a second elevator within delivery shaft 514. In another aspect, first knob 532 may be rotatable to deflect the distal end of delivery shaft 514 in a first plane, and second knob 580 may be rotatable to deflect the distal end of delivery shaft 514 in a second plane. The second plane may be approximately perpendicular to the first plane. In this aspect, control device 530, with first knob 532 and second knob 580, may allow for the deflection of the distal end in any position or direction within a semispherical range extending from the distal end of delivery shaft 514. Furthermore, control device 530, with first knob 532 and second knob 580, may allow for the deflection of the distal end in any position or direction within a range extending from the distal end of delivery shaft 514 that is greater than the semispherical range, with large deflection angles. In yet another aspect, first knob 532 may control the deflection of the distal end of delivery shaft 514, and second knob 580 may control an elevator, or vice versa. In these aspects, control device 530 includes internal braking devices, and thus does not require an external braking device that the user may actuate and/or release from outside of handle 512.

Figure 6A:
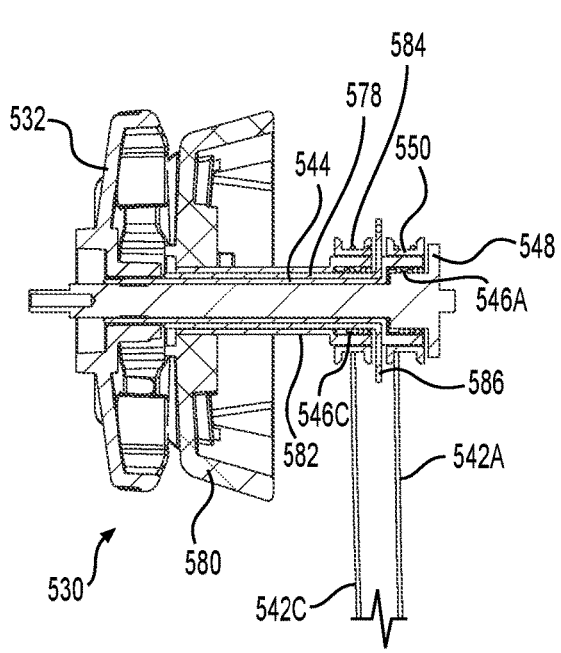
FIGS. 6A and 6B illustrate different views of another control device, according to aspects of this disclosure.
Figure 6B:
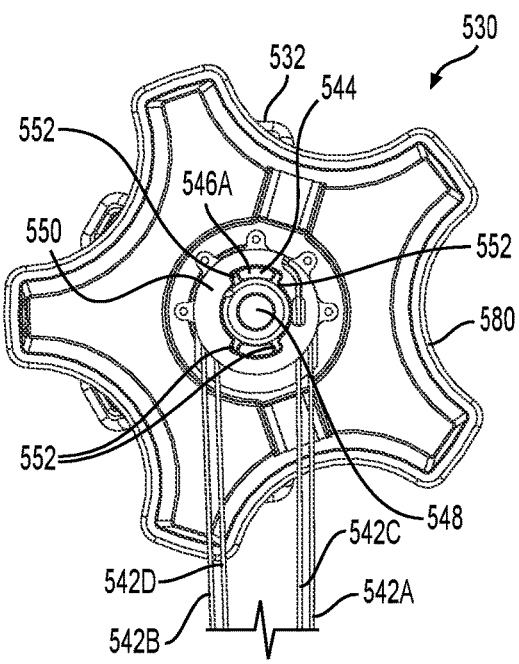

FIGS. 6A and 6B illustrate views of control device 530. FIG. 6A is a cross-sectional view of control device 530, for example, along a cross-section similar to cross-section 2B-2B in FIG. 2A. FIG. 6B is a rear view of control device 530, for example, from a position internal to handle 512 (FIGS. 5A-5C) when control device 530 is coupled to handle 512. Control device 530 includes two or more steering or control wires, for example, 542A, 542B, 542C, and 542D, which may control one or more components of delivery shaft 514, as discussed above.

As discussed above, knob 532 may be coupled to or integrally formed with a control shaft 544. Shaft 544 may include an internal lumen to receive a portion of an axle 548, and may also interact with a spool 550 to control the movement of one or more control wires, for example, first control wire 542A. Additionally, one or more spring clutches 546A may be positioned between spool 550 and a portion of axle 548 to selectively rotationally fix or lock spool 550 to axle 548.

Additionally, knob 580 may be coupled to or integrally formed with a control shaft 582. Shaft 582 may include an internal lumen to receive a portion of shaft 544, and thus also axle 548. In one aspect, a hollow axle 578 may be positioned between shaft 544 and shaft 582. Shaft 582 may also interact with a spool 584 to control the movement of one or more control wires, for example, second control wire 542B. Additionally, one or more spring clutches 546C may be positioned between spool 584 and a portion of hollow axle 578 to selectively rotationally fix or lock spool 584 to hollow axle 578. Furthermore, hollow axle 578 may include an extension portion 586. Extension portion 586 may be positioned between spool 550 and spool 584, and may help allow for spool 550 and spool 584 to be actuated and rotated separately from each other.

Shaft 544, spring clutch 546A, axle 548, and spool 550 operate to selectively lock and unlock the rotation of shaft 544 and spool 550 relative to axle 548 as discussed with respect to the corresponding structure of FIGS. 2A-2C and FIG. 3. As shown in FIG. 6B, spring clutch 546A may be positioned around axle 548, for example, between axle 548 and a spool 550. When no forces are acting on control device 530, spring clutch 546A is tightly positioned or pressed around axle 548, and helps to secure spool 550, and thus first control wire 542A, relative to axle 548, and thus relative to handle 512 and delivery shaft 514. Spring clutch 546A may include one or more legs 552. Rotating knob 532 and shaft 544 may interact with one or more of legs 552 of spring clutch 546A. For example, rotating knob 532 and shaft 544 may cause a portion of shaft 544 to contact one or more of legs 552, pushing one or more of legs 552 in a direction to unwrap or loosen spring clutch 546A. Loosening spring clutch 546A may reduce a frictional connection between spool 550 and axle 548. Furthermore, rotating knob 532 and shaft 544 may also cause a portion of shaft 544, or a portion of the one or more legs 552, to contact a portion of spool 550, which may cause spool 550 to rotate. Rotating spool 550 may then proximally retract control wire 542A to control a portion of delivery shaft 514.

Similarly, although not shown in FIGS. 6A and 6B, shaft 582 may interact with one or more legs of spring clutch 546C, for example, such that rotating knob 580 loosens spring clutch 546C, and thus reduces the frictional connection between spool 584 and hollow axle 578.

Figure 7:
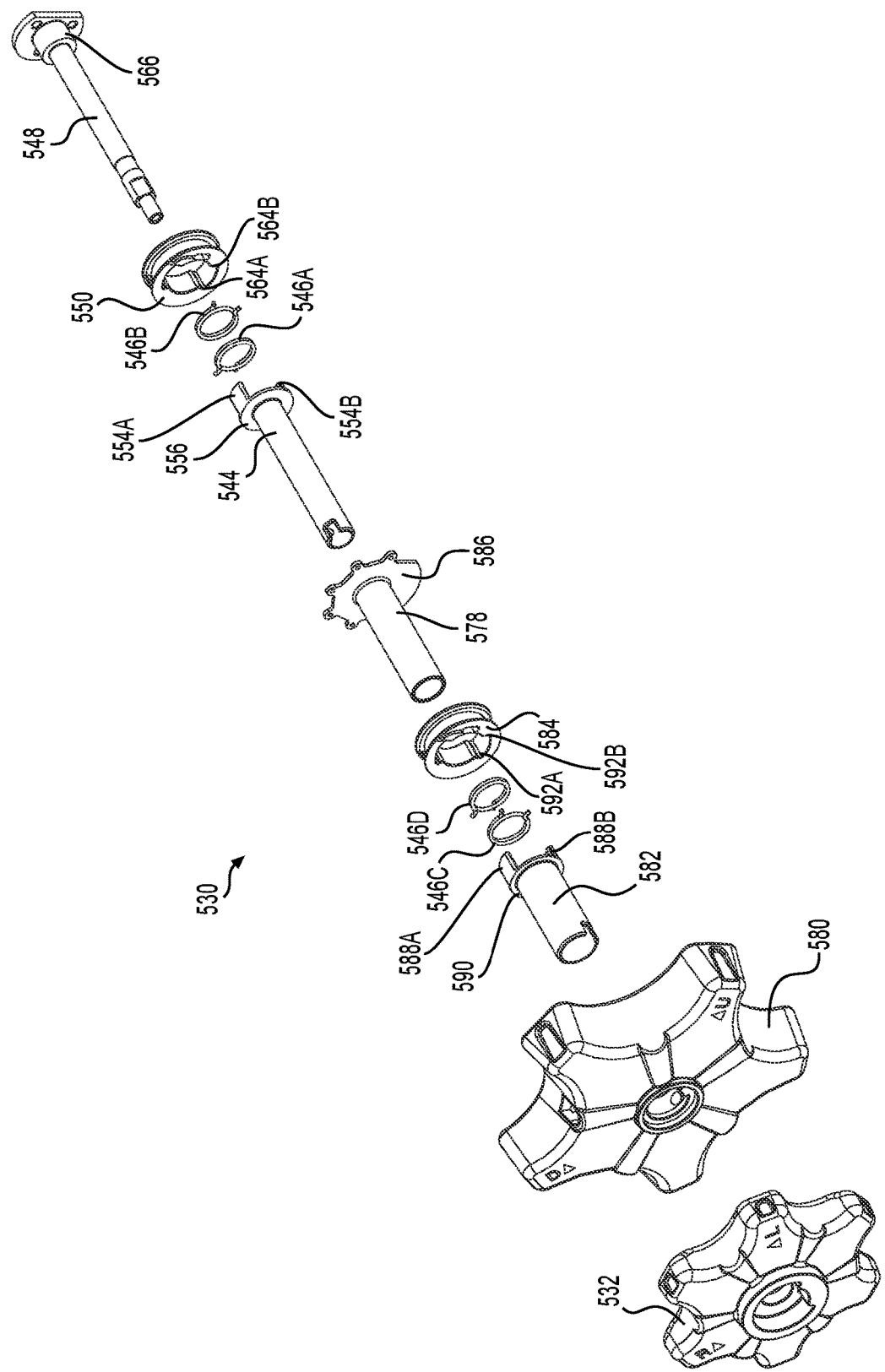
FIG. 7 illustrates an exploded view of the another control device, according to aspects of this disclosure.

FIG. 7 is an exploded view of control device 530, including knob 532, shaft 544, at least one spring clutch (i.e., two spring clutches 546A and 546B), axle 548, and spool 550. Although not shown, one or more control wires (e.g., control wires 542A and 542B) may be coupled to spool 550. In this aspect, rotating knob 532 and shaft 544 may rotate spool 550, which may control the movement of the one or more control wires to deflect or otherwise control a distal portion of the delivery shaft (not shown), similar to the interaction of knob 32, shaft 44, spring clutch 46, axle 48, spool 50, and control wires 42A, 42B, shown in FIGS. 2A-2C and 3. As discussed above, rotating knob 530 and shaft 544 may loosen one or more of spring clutches 546A or 546B. For example, shaft 544 includes one or more projections, for example, first and second projections 554A and 554B coupled to shaft 544 via a radial extension 556. Projections 554A and 554B may interact with legs of spring clutches 546A, 546B, as discussed above, to loosen spring clutches 546A, 546B, and loosen the connection between spool 550 and widened portion 566 of axle 548. Furthermore, as discussed above, the legs may interact with one or more stop surfaces (e.g., stop surfaces 564A and 564B) to rotate spool 550 to control one or more control wires (not shown).

Additionally, as shown in FIG. 7, control device 530 includes knob 580, shaft 582, at least one additional spring clutch (i.e., two spring clutches 546C and 546D), and spool 584. Although not shown, one or more control wires (e.g., control wires 542C and 542D) may be coupled to spool 584. This assembly operates in much the same way as the interaction of knob 32, shaft 44, spring clutch 46, axle 48, spool 50, and control wires 42A, 42B, shown in FIGS. 2A-2C and 3. Specifically, rotating knob 580 and shaft 582 may interact with and loosen spring clutches 546C and 546D and rotate spool 584, as discussed above. Rotating spool 584 may control the movement of the one or more control wires to deflect or otherwise control the distal portion of the delivery shaft (not shown). Moreover, hollow axle 578 may be secured to handle 512, and may help to allow for shafts 544 and 582 to rotate separately. Furthermore, hollow axle 578 may include extension portion 586, which may separate spools 550 and 584, and allow for spools 550 and 584 to rotate separately.

Moreover, rotating knob 580 and shaft 582 may loosen one or more of spring clutches 546C or 546D. For example, shaft 582 includes one or more projections, for example, first and second projections 588A and 588B, coupled to shaft 582 via a radial extension 590. Projections 588A and 588B may interact with legs of spring clutches 546C, 546D, as discussed above, to loosen spring clutches 546C, 546D and loosen the connection between spool 584 and hollow axle 578. Furthermore, as discussed above, the legs may interact with one or more stop surfaces (e.g., stop surfaces 592A or 592B) to rotate spool 584 to control one or more control wires (not shown).

Furthermore, as discussed above, external forces, for example, forces imparted on spool 550 or spool 584 by the control wires may rotate spool 550 or spool 584 to contact one or more of clutch springs 546A, 546B, 546C, 546D in such a way to tighten the one or more of clutch springs 546A, 546B, 546C, 546D. For example, the control wires may impart forces from inherent forces on delivery shaft 514 that bias delivery shaft 514 to return to an unbent or a non-deflected position, forces caused by the distal end of delivery shaft 514 contacting tissue or other material at the treatment site, etc., but these forces may cause spools 550, 584 to contact and tighten one or more of clutch springs 546A, 546B, 546C, 546D. As such, control device 530 may also help to retain a portion of delivery shaft 514 in a manipulated position.

One or more, and any combination, of the spring clutches may be incorporated in control device 530. Additionally, more than two knobs, shafts, etc. may be included on handle 512, for example, to control more than two aspects of delivery shaft. For example, three knobs may be incorporated in a control device on handle 512. First and second knobs may be configured to deflect delivery shaft 514 in two different planes, and a third knob may be configured to actuate an elevator, for example, positioned adjacent to distal opening 24 in FIGS. 1A and 1B.

Various aspects discussed herein may help to reduce the duration, costs, and/or risks of a medical procedure. For example, the control devices allow for the user to selectively manipulate one or more control wires. The control devices also lock the control wires in the selected position, and also help to prevent inadvertent movement of the control wires, for example, from forces acting on the delivery shaft. In this aspect, control devices may help to provide a brake with few, inexpensive components. Due to the spring-forces imparted by the spring clutch(es), the brake provided by the control devices automatically disengages when the knob and the shaft are rotated by user manipulation, and the brake provided by the control devices engages automatically after the user manipulation ends. For example, the user may rotate the knob to deflect the distal end of the delivery shaft. The user may let go of the knob at the rotated position, and the one or more spring clutches may automatically return to the contracted position and secure the spool to the axle. In this aspect, forces imparted on the spool from the control wires, or back pressure from the control wires, causes the one or more spring clutches to tighten and help prevent the forces imparted by the control wires from rotating the spool.

Additionally, the one or more spring clutches may be formed of a commonly available spring or wire material. Alternatively, the one or more spring clutches may be formed of stamped sheet metal, a plastic material, an injection molded clip, etc. The size, number, materials, etc. of the one or more spring clutches may also be tailored for a specific medical device or a specific application of the medical device. The amount of friction that each spring clutch can withstand before slipping may vary based on the properties of each spring clutch. However, the amount of friction that each spring clutch can withstand before slipping is also dependent on the number of wraps or coils that make up (or the longitudinal width) of the one or more spring clutches, the material properties of the wire, the amount of pre-loaded friction (e.g., how "tight" the spring is on the axle in a neutral or unactuated position) due to interference between the inner diameter of the one or more spring clutches and the outer diameter of the axle, etc. The frictional force provided to the spool may also be controlled (e.g., increased or decreased) based on the number of the spring clutches that are included around the axle. The frictional force may then provide enough holding force to prevent the delivery shaft from naturally returning to a straight or unactuated position, while also minimizing the driving force necessary for the knob and the shaft to release the one or more spring clutches and rotate the spool to actuate a portion of the delivery shaft.

The control devices may be positioned anywhere on the handle, for example, in a location that is convenient during the medical procedure. Furthermore, the control devices do not require an external braking system (braking components external to the handle body), which may help to reduce the overall size and usability of the control devices and the medical devices. Not requiring an external braking system also may help to allow for the knob(s) of the control devices to be positioned adjacent or close to the handles, which may improve the ergonomics and/or usability of the medical devices, especially for users with smaller hands. In addition, not requiring an external braking system may reduce the overall size of the handles, for example, reducing the risk that the handles may tip and/or fall off a table (e.g., during sterilization), reducing the size and/or amount of packaging necessary to package the medical devices, reducing the space necessary to store the medical devices, etc.

As mentioned, the control devices may automatically secure the control wires, and thus the controlled portion of the delivery shafts, in the selected position. Accordingly, there is no need for a user to manipulate an external brake element or otherwise lock one or more components in a position, and then manipulate the component in the locked configuration for final or smaller maneuvers, which imposes stresses on the internal components, exacerbates hand fatigue for the user, etc. Moreover, multiple control devices may be incorporated on one handle, as discussed above, in order to deflect the distal end of the delivery shaft in multiple directions, to actuate or move one or more elevators in the delivery shaft, and/or otherwise actuate a cable driven function of the medical devices.

Accordingly, various aspects discussed herein may help to improve the efficacy of treatment and/or recovery from a procedure, for example, a procedure to treat a treatment site. Various aspects discussed herein may help to reduce and/or minimize the duration of the procedure, may reduce the risks of inadvertent manipulation by the user, and/or may help reduce risks of inadvertent contact with tissue or other material during delivery, repositioning, or usage of a medical device in the procedure.

While principles of this disclosure are described herein with reference to illustrative aspects for various applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
   a handle, including an axle;
   a device shaft extending from the handle to a distal end; and
   a control device, wherein the control device is coupled to the handle and includes:
   a knob, wherein the knob is rotatable relative to the handle;
   a control shaft extending from the knob, wherein the control shaft includes a radial extension, and wherein the control shaft includes first and second projections extending from the radial extension;
   a first spring clutch and a second spring clutch, wherein each of the first and second spring clutch includes a first leg and a second leg;
   a spool, wherein the spool is rotatable relative to the axle, and wherein the spool defines first and second gaps, and wherein the first and second projections are configured to be positioned within the first and second gaps; and
   one or more wires coupled to the spool,
   wherein rotation of the knob is configured to rotate the control shaft, causing the spool to rotate and the one or more wires to move, wherein rotation of the knob in a first direction causes the first projection to contact the first leg of the first spring clutch to loosen the first spring clutch, and wherein rotation of the knob in the first direction causes the second projection to contact the first leg of the second spring clutch to loosen the second spring clutch, and
   wherein further rotation of the knob in the first direction causes (1) the first leg of the first spring clutch to contact a first stop surface of the spool adjacent the first gap, (2) the first leg of the second spring clutch to contact a second stop surface of the spool adjacent the second gap, and (3) the spool to rotate in the first direction.

2. The medical device of claim 1, wherein rotation of the knob in a second direction causes the first projection to contact the second leg of the second spring clutch to loosen the second spring clutch, and wherein rotation of the knob in the second direction causes the second projection to contact the second leg of the first spring clutch to loosen the first spring clutch, and
   wherein further rotation of the knob in the second direction causes (1) the second leg of the second spring clutch to contact a third stop surface of the spool adjacent the second gap, (2) the second leg of the first spring clutch to contact a fourth stop surface of the spool adjacent the second gap, and (3) the spool to rotate in the second direction.

3. The medical device of claim 1, wherein the first spring clutch or the second spring clutch includes at least one spring formed of a coil with two radially outward extending legs.

4. The medical device of claim 1, wherein the first spring clutch or the second spring clutch includes at least one spring with a ring-like shape that includes a partially cylindrical portion and an interaction portion, wherein the interaction portion includes a first end and a second end, wherein the first end includes a first radially outward extending leg, and wherein the second end includes two radially outward extending legs.

5. The medical device of claim 1, wherein the first spring clutch or the second spring clutch includes at least one spring with a partial ring-like shape that includes a partially cylindrical portion and an open portion, wherein the partially cylindrical portion includes two radially outward extending legs on opposing sides of the open portion.

6. The medical device of claim 1, wherein the first spring clutch or the second spring clutch includes at least one spring formed of a coil with two radially inward extending legs.

7. The medical device of claim 1, wherein the control device is a first control device, and wherein the medical device further comprises a second control device that is coaxial with the first control device, wherein the second control device includes:
a second knob, wherein the second knob is rotatable relative to the handle;
a second control shaft extending from the second knob;
at least one third spring clutch including two legs;
a second spool, wherein the second spool is rotatable relative to the axle; and
one or more second wires coupled to the second spool, wherein rotation of the second knob is configured to rotate the second control shaft, causing the at least one third spring clutch to loosen, the second spool to rotate, and the one or more second wires to move.

8. The medical device of claim 7, wherein a portion of the control shaft of the first control device is nested within the second control shaft of the second control device, and wherein the medical device further comprises:
a hollow axle separating a portion of the control shaft from the second control shaft, wherein the hollow axle is coupled to the handle and includes a radial extension that separates the spool of the first control device from the second spool of the second control device.

9. The medical device of claim 1, wherein the distal end of the device shaft is deflectable via the control device.

10. The medical device of claim 1, wherein the handle includes at least one port configured to receive a medical device, wherein the port is connected to a lumen that extends through the handle and the device shaft, and wherein the control device is configured to control an elevator positioned adjacent to the lumen at the distal end of the device shaft.

11. The medical device of claim 1, wherein the control device is positioned on a proximal portion of the handle, and wherein the medical device does not include a brake external to a body of the handle to lock the position of the knob.

12. A medical device, comprising:
a handle, including an axle;
a device shaft extending from the handle to a distal end; and
a control device, wherein the control device is coupled to the handle and includes:
a first knob, wherein the first knob is rotatable relative to the handle;
a first control shaft extending from the first knob, wherein the first control shaft includes a radial extension, and wherein the first control shaft includes first and second projections extending from the radial extension;
a first spring clutch including two legs;
a second spring clutch including two legs;
a first spool, wherein the first spool is rotatable relative to the axle, wherein the first spool defines first and second gaps, and wherein the first and second projections of the first control shaft are configured to be positioned within the first and second gaps of the first spool;
one or more first wires coupled to the first spool;
a second knob, wherein the second knob is rotatable relative to the handle;
a second control shaft extending from the second knob;
a third spring clutch including two legs;
a second spool, wherein the second spool is rotatable relative to the axle; and
one or more second wires coupled to the second spool, wherein rotation of the first knob is configured to rotate the first control shaft, causing the first projection to contact a first leg of the two legs of the first spring clutch to loosen the first spring clutch, the first spool to rotate, the one or more first wires to move, and the distal end of the device shaft to deflect in a first plane, wherein further rotation of the first knob causes (1) the first leg of the first spring clutch to contact a first stop surface of the first spool adjacent the first gap, (2) a first leg of the two legs of the second spring clutch to contact a second stop surface of the first spool adjacent the second gap, and (3) the first spool to rotate, and
wherein rotation of the second knob is configured to rotate the second control shaft, causing the third spring clutch to loosen, the second spool to rotate, the one or more second wires to move, and the distal end of the device shaft to deflect in a second plane different from the first plane.

13. The medical device of claim 12,
wherein the legs of the first spring clutch are positioned between the first or second projection of the first control shaft and edges of the first or second gap of the first spool, and wherein the legs of the second spring clutch are positioned between a first or second projection of the second control shaft and edges of a first or second gap of the second spool.

14. The medical device of claim 12, wherein the first plane and the second plane are perpendicular.

15. The medical device of claim 12, wherein a portion of the first control shaft is nested within the second control shaft, and
wherein the axle separates a portion of the first control shaft from the second control shaft, wherein the axle is coupled to the handle and includes a radial extension that separates the first spool from the second spool.

16. The medical device of claim 12, wherein the first or second spring clutch includes at least one spring formed of a coil with two radially outward extending legs.

17. The medical device of claim 12, wherein the first or second spring clutch includes at least one spring with a ring-like shape that includes a partially cylindrical portion and an interaction portion, wherein the interaction portion includes a first end and a second end, wherein the first end includes a first radially outward or radially inward extending leg, and wherein the second end includes two radially outward or radially inward extending legs.

18. The medical device of claim 12, wherein rotation of the first knob in a second direction causes the first projection of the first control shaft to contact a second leg of the two legs of the second spring clutch to loosen the second spring clutch, and wherein rotation of the first knob in the second direction causes the second projection to contact a second leg of the two legs of the first spring clutch to loosen the first spring clutch, and wherein further rotation of the first knob in the second direction causes (1) the second leg of the second spring clutch to contact a third stop surface of the first spool adjacent the second gap, (2) the second leg of the first spring clutch to contact a fourth stop surface of the first spool adjacent the second gap, and (3) the first spool to rotate in the second direction.

19. A medical device handle, comprising:
an axle, wherein the axle is fixed to the handle;
a control device, wherein the control device includes:
    a first knob, wherein the first knob is rotatable relative to the handle;
    a first control shaft extending from the first knob, wherein the first control shaft includes a radial extension, and wherein the first control shaft includes first and second projections extending from the radial extension;
    a first spring clutch including two legs;
    a second spring clutch including two legs;
    a first spool, wherein the first spool is rotatable relative to the axle, wherein the first spool defines first and second gaps, and wherein the first and second projections of the first control shaft are configured to be positioned within the first and second gaps of the first spool;
    one or more first wires coupled to the first spool;
    a second knob, wherein the second knob is rotatable relative to the handle;
    a second control shaft extending from the second knob;
    a third spring clutch including two legs;
    a second spool, wherein the second spool is rotatable relative to the axle; and
    one or more second wires coupled to the second spool,
wherein rotation of the first knob is configured to rotate the first control shaft, causing the first projection of the first control shaft to contact a first leg of the two legs of the first spring clutch to loosen the first spring clutch, the first spool to rotate, and the one or more first wires to move,
wherein further rotation of the first knob causes (1) the first leg of the first spring clutch to contact a first stop surface of the first spool adjacent the first gap, (2) a first leg of the two legs of the second spring clutch to contact a second stop surface of the first spool adjacent the second gap, and (3) the first spool to rotate, and
wherein rotation of the second knob is configured to rotate the second control shaft, causing the third spring clutch to loosen, the second spool to rotate, and the one or more second wires to move.

20. The medical device handle of claim 19, wherein a portion of the first control shaft is nested within the second control shaft, and wherein the medical device handle further comprises:
    a hollow axle separating a portion of the first control shaft from the second control shaft, wherein the hollow axle is coupled to the handle and includes a radial extension that separates the first spool from the second spool.

* * * * *